US012029722B2

(12) United States Patent
Chistov

(10) Patent No.: US 12,029,722 B2
(45) Date of Patent: *Jul. 9, 2024

(54) DOSAGE DELIVERY FILM

(71) Applicant: Spartak LLC, Manalapan, NJ (US)

(72) Inventor: Sergey Y. Chistov, Miami, FL (US)

(73) Assignee: Spartak LLC, Manalapan, NJ (US)

( * ) Notice: Subject to any disclaimer, the term of this patent is extended or adjusted under 35 U.S.C. 154(b) by 263 days.

This patent is subject to a terminal disclaimer.

(21) Appl. No.: 17/103,518

(22) Filed: Nov. 24, 2020

(65) Prior Publication Data

US 2021/0077456 A1 Mar. 18, 2021

Related U.S. Application Data

(63) Continuation of application No. 16/404,581, filed on May 6, 2019, now Pat. No. 10,857,125, which is a continuation of application No. 16/058,669, filed on Aug. 8, 2018, now Pat. No. 10,307,394, which is a continuation of application No. 15/611,581, filed on Jun. 1, 2017, now Pat. No. 10,058,531.

(51) Int. Cl.
| | |
|---|---|
| *A61K 9/00* | (2006.01) |
| *A61K 9/107* | (2006.01) |
| *A61K 9/70* | (2006.01) |
| *A61K 31/05* | (2006.01) |
| *A61K 31/343* | (2006.01) |
| *A61K 31/352* | (2006.01) |
| *A61K 31/353* | (2006.01) |
| *A61K 47/06* | (2006.01) |
| *A61K 47/08* | (2006.01) |
| *A61K 47/10* | (2017.01) |
| *A61K 47/26* | (2006.01) |
| *A61K 47/40* | (2006.01) |

(52) U.S. Cl.
CPC ............ *A61K 31/353* (2013.01); *A61K 9/006* (2013.01); *A61K 9/107* (2013.01); *A61K 9/1075* (2013.01); *A61K 9/7007* (2013.01); *A61K 31/05* (2013.01); *A61K 31/343* (2013.01); *A61K 31/352* (2013.01); *A61K 47/06* (2013.01); *A61K 47/08* (2013.01); *A61K 47/10* (2013.01); *A61K 47/26* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 4,719,239 A | 1/1988 | Muller et al. | |
| 4,764,378 A | 8/1988 | Keith et al. | |
| 5,070,081 A | 12/1991 | Majid et al. | |
| 5,374,304 A | 12/1994 | Frische et al. | |
| 6,194,379 B1 | 2/2001 | McEwen et al. | |
| 6,383,513 B1 | 5/2002 | Watts et al. | |
| 7,423,026 B2 | 9/2008 | Järvinen et al. | |
| 7,592,328 B2 | 9/2009 | Jarho et al. | |
| 7,897,080 B2 | 3/2011 | Yang et al. | |
| 7,910,031 B2 | 3/2011 | Yang et al. | |
| 7,972,618 B2 | 7/2011 | Fuisz et al. | |
| 8,623,401 B2 | 1/2014 | Modi | |
| 8,652,378 B1 | 2/2014 | Yang et al. | |
| 8,703,177 B2* | 4/2014 | Finn .......................... | A61P 1/00 |
| | | | 424/443 |
| 8,735,374 B2 | 5/2014 | Zerbe et al. | |
| 8,808,734 B2 | 8/2014 | Winnicki | |
| 9,044,390 B1 | 6/2015 | Speier | |
| 9,125,434 B2 | 9/2015 | Fuisz | |
| 9,186,386 B2 | 11/2015 | Speier | |
| 9,248,146 B2 | 2/2016 | Barnhart et al. | |
| 9,402,908 B2 | 8/2016 | Kabanov et al. | |
| 9,649,349 B1 | 5/2017 | Tucker et al. | |
| 10,058,531 B1* | 8/2018 | Chistov .................. | A61K 47/06 |
| 10,307,394 B2* | 6/2019 | Chistov .................. | A61K 47/40 |
| 10,857,125 B2* | 12/2020 | Chistov .................. | A61K 47/08 |
| 11,096,892 B2* | 8/2021 | Xu .......................... | A61K 31/192 |
| 2004/0047930 A1 | 3/2004 | Webbe et al. | |
| 2005/0191343 A1 | 9/2005 | Liang | |
| 2007/0281003 A1 | 12/2007 | Fuisz et al. | |
| 2009/0105132 A1 | 4/2009 | Jarho et al. | |
| 2011/0028431 A1 | 2/2011 | Zerbe et al. | |

(Continued)

FOREIGN PATENT DOCUMENTS

| | | |
|---|---|---|
| DE | 102010009071 | 10/2011 |
| DE | 112004002828 | 10/2015 |

(Continued)

OTHER PUBLICATIONS

Bergeron et al. polydimethysiloxane (PDMS) based anti-foams, Colloids and Surfaces, A:Physicochemical and engineering aspect, p. 103-120. 1997). (Year: 1997).*

Polyethylene Glycol. Wikipedia Sep. 14, 2022 12 pages (Year: 2022).*

CanniMed. CTT Pharmaceutical Holdings to License to CanniMed Ltd. Novel Cannabis Orally Dissolvable Thing Film (ODF) Water Drug Delivery Technology for North American Markets. Website, https://www.cannimed.ca, originally downloaded Dec. 1, 2016, 4 pages.

(Continued)

*Primary Examiner* — Lakshmi S Channavajjala
(74) *Attorney, Agent, or Firm* — Craig R. Miles; CR MILES P.C.

(57) ABSTRACT

A dosage delivery film composition containing a botanical drug substance formable into a bioerodible dosage delivery film, the dosage delivery film composition including: (i) one or more of: a polymer, a plasticizer, a defoamer, or an antioxidant; (ii) a cannabinoid-cyclodextrin-terpene complex or a cannabinoid-terpene-surfactant micelle, and (iii) optionally, one or more of: a taste mask, a vasodilator, or a lipophilic vehicle to transport the botanical drug substance across the mucous membrane.

32 Claims, No Drawings

(56) References Cited

U.S. PATENT DOCUMENTS

| | | |
|---|---|---|
| 2013/0295026 A1 | 11/2013 | Viernstein et al. |
| 2015/0297556 A1 | 10/2015 | Smith |
| 2016/0058866 A1 | 3/2016 | Sekura et al. |
| 2016/0175199 A1 | 6/2016 | Yang et al. |
| 2016/0279071 A1 | 9/2016 | Park et al. |
| 2016/0317462 A1 | 11/2016 | Sapkal et al. |

FOREIGN PATENT DOCUMENTS

| | | |
|---|---|---|
| EP | 1802274 B1 | 9/2008 |
| EP | 2286793 A2 | 2/2011 |
| EP | 2292211 A2 | 3/2011 |
| EP | 2298283 A2 | 3/2011 |
| EP | 2298284 A2 | 3/2011 |
| EP | 2311475 A2 | 4/2011 |
| EP | 2524695 A1 | 11/2011 |
| EP | 1385595 B2 | 5/2012 |
| EP | 1536810 B1 | 8/2012 |
| EP | 1361864 B2 | 12/2013 |
| GB | 2 355 405 | 4/2001 |
| WO | 02/24145 A2 | 3/2002 |
| WO | 02/064109 A2 | 8/2002 |
| WO | 02/089945 A2 | 11/2002 |
| WO | 2004/016277 A2 | 2/2004 |
| WO | 2006/037981 A1 | 4/2006 |
| WO | 2010/004355 A2 | 1/2010 |
| WO | 2010/050794 A1 | 5/2010 |
| WO | 2010/064891 A1 | 6/2010 |
| WO | 2010/150245 A1 | 12/2010 |
| WO | 2011/083397 A1 | 7/2011 |
| WO | 2011/083398 A2 | 7/2011 |
| WO | 2014/000803 A1 | 1/2014 |
| WO | 2015/068052 A2 | 5/2015 |

OTHER PUBLICATIONS

MarketWired. MediJane Holdings Finalizes New Medical Cannabis Medi-Strips Product Line. Website, http://www.marketwired.com, originally downloaded Dec. 1, 2016, 2 pages.

Russo. Taming THC: potential cannabis synergy and phytocannabinoid-terpenoid entourage effects. British J Pharmacol, Aug. 2011, 163(7):1344-1364.

Sharma et al. Fast Dissolving Oral Films Technology: A Recent Trend for an Innovative Oral Drug Delivery System. Int J Drug Delivery, Oct. 2015, 67(2):60-76.

U.S. Appl. No. 15/611,581, filed Jul. 17, 2017.

U.S. Appl. No. 16/058,669, filed Aug. 8, 2018.

PCT International Patent Application No. PCT/US18/31398; International Search Report and Written Opinion of the International Searching Authority dated Sep. 14, 2018, 12 pages.

U.S. Appl. No. 16/404,581, filed May 6, 2019.

Corresponding European Patent Application No. EP 18810694.2; Supplementary European Search Report dated Oct. 12, 2020. 8 pages.

Astruc-Diaz et al. In Vivo Efficacy of Enabling Formulations Based on Hydroxypropyl-B-Cyclodextrins, Micellar Preparation, and Liposomes for the Lipophilic Cannabinoid CB2 Agonist, MDA7. Journal of Pharmaceutical Sciences, Feb. 2013, 102(2):352-364.

* cited by examiner

DOSAGE DELIVERY FILM

This United States patent application is a continuation of U.S. patent application Ser. No. 16/404,581, filed May 6, 2019, now U.S. Pat. No. 10,857,125, issued Dec. 8, 2020, which is a continuation of U.S. patent application Ser. No. 16/058,669, filed Aug. 8, 2018, now U.S. Pat. No. 10,307,394, issued Jun. 4, 2019, which is a continuation of U.S. patent application Ser. No. 15/611,581, filed Jun. 1, 2017, now U.S. Pat. No. 10,058,531, issued Aug. 28, 2018, each hereby incorporated by reference herein.

I. FIELD OF THE INVENTION

Generally, a dosage delivery film for oral delivery of a dosage of a botanical drug substance. Specifically, a dosage delivery film composition containing a botanical drug substance formable into a bioerodible dosage delivery film, the dosage delivery film composition including: (i) one or more of: a polymer, a plasticizer, a defoamer, or an antioxidant; (ii) a cannabinoid-cyclodextrin-terpene complex or a cannabinoid-terpene-surfactant micelle, and (iii) optionally, one or more of: a taste mask, a vasodilator, or a lipophilic vehicle to transport the botanical drug substance across the mucous membrane.

II. BACKGROUND OF THE INVENTION

The administration, or method of delivery, of pharmaceutically active agents can be by oral administration utilizing syrups, tablets, and dosage delivery films. Of these drug delivery methods, dosage delivery films have proven particularly effective for a class of patients with phagophobia, a fear of swallowing, pnigophobia, a fear of choking, and dysphagia, difficulty swallowing. In dosage delivery film applications, a pharmaceutically active agent can be contained in a dosage delivery film which dissolves within the mouth of the patient, delivering the pharmaceutically active agent buccally or sublingually, obviating the need to swallow the pharmaceutically active agent. Further, the use of dosage delivery films may promote greater bioavailability of the pharmaceutically active agent, because the pharmaceutically active agent can be delivered directly to the capillaries of the mouth, and thereby, the bloodstream. This method of delivery avoids the need for the pharmaceutically active agent to be absorbed by the stomach, and further avoids the first-pass effect of the liver, which can reduce bioavailability of the drug when given in tablet or liquid form.

With the legalization of marijuana in several states and the emerging promise of extracts from various species of *Cannabis* as natural pharmaceutical active agents, methods of delivery of the *Cannabis* extracts are of interest. Cannabinoid extracts derived from species of *Cannabis* have been shown to be effective treatments for glaucoma, epilepsy, Dravet's syndrome, cancer, anxiety, Alzheimer's, muscle spasms, pain from multiple sclerosis, inflammatory bowel disease, pain from arthritis, lupus, Parkinson's disease, post-traumatic stress disorder, pain and nausea accompanying chemotherapy, anorexia, and drug dependency and withdrawal. Currently, cannabinoids are often ingested as a component of an edible composition, whether as solids or liquids, or by inhalation of smoke from burning the leaves of or extracts obtained from the *Cannabis* plant.

Each of these methods of delivery can have certain limitations or drawbacks. Inhalation of the smoke can irritate the lungs, leading to adverse health effects. Ingestion can reduce efficacy due to malabsorption across the gastrointestinal tract, the first-pass effect of the liver, or molecular modifications occurring during these processes. These limitations may be reduced or inapplicable to dosage delivery films, which can be an effective method for delivering cannabinoids.

Therefore, there would be an advantage in dosage delivery compositions which can entrain a greater weight percentage of cannabinoid by comparison to conventional dosage delivery compositions while remaining formable for production of a dosage delivery film which effectively delivers cannabinoids buccally or sublingually to increase bioavailability of the pharmaceutically active agent.

III. SUMMARY OF THE INVENTION

Accordingly, a broad object of the invention can be to provide one or more embodiments of a first or second carrier of a cannabinoid, the first carrier in the form of a micelle including a hydrophobic core of about five to about fifty molecules of a cannabinoid disposed in a hydrophilic shell of a surfactant, the micelle having a diameter of between about 40 nm to about 100 nm ("cannabinoid micelle"), and the second carrier in the form of a cannabinoid-terpene-cyclodextrin complex ("CTC complex").

Another broad object of the invention can be to provide one or more embodiments of a dosage delivery film composition into which a botanical drug substance can be introduced and thereafter formed into a dosage delivery film which bioerodes upon oral administration to buccally or sublingually deliver a dosage of the botanical drug substance, such as a cannabinoid, to the blood stream. The dosage delivery film composition including or consisting of: (i) one or more of a polymer, a plasticizer, a defoamer, or an antioxidant; and (ii) optionally, one or more of: a taste mask, a vasodilator, or a lipophilic vehicle to transport the botanical drug substance across the mucous membrane.

Another broad object of the invention can be to provide one or more embodiments of a dosage delivery film formed from a dosage delivery film composition including an amount of a CTC complex or an amount of a cannabinoid-terpene-surfactant micelle, or combinations thereof, which bioerodes upon oral administration to buccally or sublingually deliver a dosage of a botanical drug substance, such as a cannabinoid, to the blood stream. The dosage delivery film including or consisting of: (i) one or more of a polymer, a plasticizer, a defoamer, or an antioxidant; (ii) a cannabinoid-cyclodextrin-terpene complex or a cannabinoid-terpene-surfactant micelle or combinations thereof; and (iii) optionally, one or more of: a taste mask, a vasodilator, or a lipophilic vehicle to transport the botanical drug substance across the mucous membrane.

Naturally, further objects of the invention are disclosed throughout other areas of the specification, drawings, photographs, and claims.

IV. DETAILED DESCRIPTION OF THE INVENTION

Generally, a dosage delivery film for oral delivery of a dosage of a botanical drug substance. Specifically, a dosage delivery film composition containing a botanical drug substance formable into a bioerodible dosage delivery film, the dosage delivery film composition including: (i) one or more of a polymer, a plasticizer, a defoamer, or an antioxidant; (ii) a cannabinoid-terpene-cyclodextrin complex or a cannabinoid-terpene-surfactant micelle (iii) optionally, one or more of: a taste mask, a vasodilator, or a lipophilic vehicle to facilitate transport of the botanical drug substance across the mucous membrane.

"A" or "an" entity means one or more of that entity; for example, "a polymer" refers to one or more polymers or at least one polymer. As such, the terms "a" or "an", "one or more" and "at least one" can be used interchangeably herein. Furthermore, the language "selected from the group consisting of" refers to one or more of the elements in the list that follows, including combinations of two or more of the elements.

"About" means that ranges may be expressed as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. In the context of such a numerical value or range "about" means plus or minus 10% of the numerical value or range recited or claimed unless otherwise specified, or the values within the range are incrementally divided into lesser percentage between ranges or values.

"Average molecular weight" for purposes of this invention means the number average molecular weight of all of the polymer chains in a polymer, calculated as $\Sigma N_i M_i / \Sigma N_i$, where $N_i$ is the number of polymer chains having a particular mass, and Mi is the particular mass for those molecules.

"Bioerodible" for purposes of this invention means the ability of a material to break down within the physiological environment of the mouth by one or more physical, chemical, or cellular processes.

"Botanical drug substances" for the purposes of this invention means an extract which fulfils the definition of a "botanical drug substance" provided in the *Guidance for Industry Botanical Drug Products*, June 2004, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes."

"Cannabinoid" for the purposes of this invention means a class of chemical compounds that act on cannabinoid receptors on cells that repress neurotransmitter release in the brain, the cannabinoid receptors including the endocannabinoids, phytocannabinoids, synthetic cannabinoids, and cannabidiol, or combinations thereof.

"Combination or combining" for the purposes of this invention means any method of putting two or more materials together. Such methods include, but are not limited to, mixing, blending, commingling, concocting, homogenizing, incorporating, intermingling, fusing, joining, shuffling, stirring, coalescing, integrating, confounding, joining, uniting, or the like.

"Complex" for the purposes of this invention means a molecular entity formed by chemical association involving two or more component molecular entities.

"Dosage delivery film" for the purposes of this invention means a film containing a botanical drug substance bioerodible upon oral administration to deliver the botanical drug substance to the mucous membrane of the oral cavity.

"Dosage delivery film composition" for purposes of this invention means a composition containing a botanical drug substance formable into dosage delivery film and without limitation to the breadth of the foregoing formable by manufacturing processes such as solvent casting, semisolid casting, hot-melt extrusion, solid-dispersion extrusion, rolling, or other similar methods of manufacture.

"Equivalent" for the purposes of this invention means a drug or chemical containing similar amounts of the same ingredients as another drug or chemical or having similar chemical structures, properties or functions to another drug or chemical.

"Micelle" for the purposes of this invention means an aggregate of molecules having both polar or charged groups or molecules and nonpolar regions or molecules, where the polar or ionic groups or molecules form an outer shell in contact with a solution, and the nonpolar region or molecules are sequestered on the interior of the shell.

"Oral" for the purposes of this invention means the cavity of the mouth.

"Terpene" for the purposes of this invention means a hydrocarbon or derivative thereof, whether found as a natural product or biosynthesized by oligomerization of isoprene units. A terpene can be acyclic, monocyclic, bicyclic, or multicyclic.

Embodiments include a dosage delivery film which contains a dosage of a botanical drug substance which orally bioerodes for mucosal, buccal or sublingual delivery of the botanical drug substance. In particular embodiments, the botanical drug substance can be a cannabinoid associated with a carrier. A first carrier can be cyclodextrin which associates with the cannabinoid as cannabinoid-cyclodextrin complexes ("CB-CD complex"). In particular embodiments, the CB-CD complex can further include or consist of a terpene in a cannabinoid-cyclodextrin-terpene complex ("CTC complex"). A second carrier can be a surfactant which associates with the cannabinoid as a cannabinoid-terpene surfactant micelle ("cannabinoid micelle"). The CB-CD complex, the CTC complex, or the cannabinoid micelle can be discretely prepared or isolated and thereafter associated with the dosage delivery film composition, or as to particular embodiments, can be prepared as combinations of the CB-CD complex, the CTC complex, and the cannabinoid-terpene micelle, and such combination associated with the dosage delivery film composition which can be formed into the dosage delivery film.

Embodiments of the CTC complex, can include, consist essentially of or consist of a cannabinoid, a cyclodextrin, and a terpene. The CTC complex can be formed by combining an amount of a cannabinoid, an amount of a cyclodextrin, and an amount of one or more terpenes in a solvent. The solvent can, but need not necessarily, be ethanol or water. The CTC complex, upon formation and depending on the solvent(s), can remain in solution or precipitate out from the solution as a solid and be collected by filtering or the solution can be lyophilized to yield the CTC complex as a solid.

The cannabinoid can be selected from the group including or consisting of: cannabinol, cannabinolic acid, Δ(9)-tetrahydrocannabinol, Δ (9)-tetrahydrocannabinolic acid, Δ(9)-cannabidiol, Δ(9)-tetrahydrocannabidiolic acid, Δ(8)-tetrahydrocannabinol, Δ(8)-tetrahydrocannabinolic acid, Δ(8)-tetrahydrobannabidiol, Δ(8), tetrahydrocannacbidiolic acid, Δ(9)-tetrahydrocannabivarin, cannabigerol, cannabidigerolic acid, cannabichromene, cannabichromenic acid, cannabicyclol, cannabicyclolic acid, cannabielsoin, cannabitriol, nabilone, equivalents, or combinations thereof.

The cyclodextrin can be selected from the group including or consisting of: hydroxypropyl-β-cyclodextrin, sulfobutylether-β-cyclodextrin, maltosyl-β-cyclodextrin, dimethyl-β- cyclodextrin, trimethyl-β-cyclodextrin, randomly methylated-β-cyclodextrin, equivalents, or combinations thereof.

The terpene can be selected from the group including or consisting of: alpha-pinene, beta-pinene, myrcene, limonene, carophyllene, linalool, alpha bisabolol, delta 3 carene, borneol, eucalyptol, terpineol, camphene, nerolidol, terpinolene, valencene, humulene, geraniol, phellandrene, fenchol, phytol, sabinene, camphor, menthol, isoborneol, cedrane, guaiol, isopulegol, geranyl acetate, cymene, pulegon, citral, equivalents, or combinations thereof.

Now referring primarily to Table 1, particular embodiments of a CTC complex comprising, consisting essentially of, or consisting of a cannabinoid, a β-cyclodextrin and a terpene can be prepared as further described below.

TABLE 1

Cannabinoid- Terpene-Cyclodextrin Complex.

| Ingredient | Percentage wt/wt |
|---|---|
| Cannabinoid | about 19% to about 50% |
| β-cyclodextrin | about 50% to about 80% |
| Terpene | about 0.1% to about 5% |

As to particular embodiments of the CB-CD complex the ratio of cannabinoid associated with β-cyclodextrin weight to weight ("wt/wt") can be between about 1:1 to about 1:4 (about 20 percent by weight ("wt %") to about 50 wt %). As to particular embodiments of the CTC complex the ratio of cannabinoid associated with β-cyclodextrin weight to weight ("wt./wt.") can be between about 1:1 to about 1:4 (about 19 wt % to about 50 wt %) with the terpene being about 0.1 wt % to about 5 wt %. As to particular embodiments, the cannabinoid can be about 19 wt %, the β-cyclodextrin about 76 wt %, and the terpene about 5 wt %.

As to particular embodiments, the ratio of cannabinoid associated with β-cyclodextrin weight to weight can be selected from the group including or consisting of: about 1:1.5, about 1:2.0, about 1:2.5, about 1:3.0, and about 1:3.5, and combinations thereof.

As to particular embodiments, the amount of terpene, wt %, can be selected from the group consisting of: about 0.2% to about 2.0%, about 1.5% to about 2.5%, about 2.0% to about 3.0%, about 2.5% to about 3.5%, about 3.0% to about 4.0%, about 3.5% to about 4.5%, about 4.0% to about 4.9%. Because the cannabinoids or the terpenes can be isolated and purified and combined in pre-selected amounts, the amount of terpene or combinations of terpenes in the CTC complex can be adjusted in fine incremental gradation across the described ranges of the cannabinoid and terpene to adjust the pharmacological effect of the CTC complex.

In particular embodiments, the concentration of cannabinoid in solution, whether as a CB-CD complex or CTC complex can be about 10 milligrams per milliliter (mg/mL) to about 30 mg/mL. In other particular embodiments, the concentration of cannabinoid in solution can be selected from the group including or consisting of: about 10.5 mg/mL to about 15 mg/mL, about 12.5 mg/mL to about 17.5 mg/mL, about 15 mg/mL to about 20 mg/mL, about 17.5 mg/mL to about 22.5 mg/mL, about 20 mg/mL to about 25 mg/mL, about 22.5 mg/mL to about 27.5 mg/mL, and about 25 mg/mL to about 29.5 mg/mL, or combinations thereof.

Embodiments of the cannabinoid micelles, can include, consist essentially of, or consist of a cannabinoid, a terpene and a surfactant, the cannabinoid and terpene being described above. The cannabinoid micelles can be formed by combining an amount of a cannabinoid, an amount of terpene, and an amount of a surfactant in a solvent. The solvent can, but need not necessarily, be an alcohol such as ethanol. The cannabinoid micelle, upon formation and depending on the solvent(s), can remain in solution or precipitate out from the solution as a solid for collection by filtering, or the solution can be lyophilized to yield the cannabinoid micelle as a solid.

The surfactant can be selected from the group including or consisting of: monoglycerides, diglycerides, polyethylene glycol sorbitan fatty acid esters; polyethylene glycol alkyl ethers, phospholipids, hydrophilic derivatives of phospholipids, ethoxylated castor oil (e.g., polyoxyethylene (40) castor oil, polyoxyethylene (60) castor oil) corn glycerides, vitamin E, polyoxyethylene alkyl ethers, polyethylene glycol glycerol fatty acid esters, polyoxyethylene sorbitan fatty acid esters, polyethylene glycol sorbitan monooleate (TWEEN® 80), polysorbate-80, a nonionic surfactant, a cationic surfactant, an anionic surfactant, an amphoteric surfactant, equivalents, or combinations thereof.

Now referring primarily to Table 2, particular embodiments of cannabinoid micelle comprising, consisting essentially of, or consisting of a cannabinoid, a surfactant, and a terpene can be prepared as further described below.

TABLE 2

Cannabinoid Micelle Composition.

| Ingredient | Percentage wt/wt |
|---|---|
| Cannabinoid | about 20% to about 45% |
| Surfactant | about 50% to about 80% |
| Terpene | about 0.1% to about 5% |

The cannabinoid micelles can form as a hydrophobic core of about five to about fifty molecules of a cannabinoid (whether homogenous or heterogeneous mixture thereof) along with the terpene (whether homogenous or heterogeneous mixture thereof) surrounded by a hydrophilic shell of the surfactant.

The diameter of each cannabinoid micelle depending on the type and number of molecules of cannabinoid and terpene included in the hydrophobic core can be about 40 nanometers ("nm") to about 100 nm. In further embodiments, the diameter of the cannabinoid micelle can be selected from the group including or consisting of about 41 nm to about 45 nm, about 42.5 nm to about 47.5 nm, about 45 nm to about 50 nm, about 47.5 nm to about 52.5 nm, about 50 nm to about 55 nm, about 52.5 nm to about 57.5 nm, about 55 nm to about 60 nm, about 57.5 nm to about 62.5 nm, about 60 nm to about 65 nm, about 62.5 nm to about 67.5 nm, about 65 nm to about 70 nm, about 67.5 nm to about 72.5 nm, about 70 nm to about 75 nm, about 72.5 nm to about 77.5 nm, about 75 nm to about 80 nm, about 77.5 nm to about 82.5 nm, about 80 nm to about 85 nm, about 82.5 nm to about 87.5 nm, about 85 nm to about 90 nm, about 87.5 nm to about 92.5 nm, about 90 nm to about 95 nm, about 92.5 nm to about 97.5 nm, and about 95 nm to about 99 nm, or combinations thereof.

The relative weight percentages of the cannabinoid, terpene, and surfactant will vary depending upon the relative size of the cannabinoid-terpene micelles formed and the number of cannabinoid molecules and terpene molecules stationed within the hydrophobic core of the micelle. Accordingly, a finely graded series of weight percentages for each of the cannabinoid, terpene, and surfactant across the ranges of Table 2 can be achieved in the cannabinoid micelle.

In particular embodiments, the concentration of cannabinoid in solution, as a cannabinoid micelle, will vary depending on the relative size of the cannabinoid micelle and the number of cannabinoid molecules and terpene molecules stationed within the hydrophobic core. The concentration of cannabinoid can be about 10 milligrams per milliliter (mg/mL) to about 30 mg/mL. In other particular embodiments, the concentration of cannabinoid in solution can be selected from the group including or consisting of: about 10.5 mg/mL to about 15 mg/mL, about 12.5 mg/mL to about 17.5 mg/mL, about 15 mg/mL to about 20 mg/mL, about 17.5 mg/mL to about 22.5 mg/mL, about 20 mg/mL to about 25 mg/mL, about 22.5 mg/mL to about 27.5 mg/mL, and about 25 mg/mL to about 29.5 mg/mL, or combinations thereof.

As to particular embodiments, the CB-CD complex, CTC complex and the cannabinoid micelle can concurrently occur in solution. As to particular embodiments, the CB-CD complex or CTC complex can be further associated with the cannabinoid micelles to form larger complexes.

Now referring primarily to Tables 3 and 4, embodiments of a dosage delivery film composition can be formed into a dosage delivery film containing a botanical drug substance which can include one or more of: a polymer, a plasticizer, a defoamer, or an antioxidant, and water. In particular embodiments, the dosage delivery film composition can further include one or more of: a vasodilator, a lipophilic carrier, or a taste mask. Advantages of particular embodiments of the dosage delivery film composition can be that a greater weight percentage of cannabinoid can be admixed with the drug delivery film composition as compared to conventional dosage delivery film compositions while still maintaining composition properties or characteristics that allow the drug delivery film composition, including the admixed cannabinoid, to be formed into a dosage delivery film which may utilize conventional film forming equipment, as above described. As compared to conventional drug delivery film compositions per unit volume, a greater weight percent cannabinoid of about 5% to about 15% per unit volume can be achieved utilizing embodiments of the drug delivery film compositions from which a drug delivery film can be formed in substantial uniform thickness of about 50 micrometers ("μm") to about 150 μm and cut to provide a dosage delivery film a few square centimeters in area, the area varying based on the dosage to be delivered. As to particular embodiments the greater weight percent cannabinoid contained in the dosage delivery film composition can be pre-selected in incremental fine gradation across the range of about 5% to about 15% to achieve particular pharmaceutical efficacy or effects in formed dosage delivery film. As to particular embodiments the greater weight percent can be selected from the group including or consisting of: about 5.5% to about 7.5%, about 6.25% to about 8.75%, about 7.5% to about 10%, about 8.75% to about 11.25%, about 10% to about 12.5%, about 11.25% to about 13.75%, and about 12.5% to about 14.5%, or combinations thereof.

Polymers are macromolecules having a molecular chain of a number of monomers chemically linked together. The sequence of monomers can be a series of more than one type of monomer (also referred to as "a block copolymer"). The polymer can be a heteropolymer, branched polymer, or charged polymer. The polymers in accordance with embodiments of the dosage delivery film composition can be digestible, non-toxic polymers. Various characteristics can be imparted to the dosage delivery film depending upon the polymer(s) utilized in preparation of the dosage delivery film composition, whether utilizing one type or molecular structure of polymer, or combining a plurality of polymers of different types or molecular structures. The characteristics that can be imparted or altered in the drug delivery film can be drug release profiles, plasticity, mechanical strength such as Young's modulus, percent elongations, tensile strength, tear resistance, texture, viscosity, mucoadhesive properties, and other like properties.

Illustrative examples of the polymer(s) suitable for use in embodiments of the dosage delivery film composition can include or consist of: polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, ethyl cellulose, hydroxypropyl ethyl cellulose, cellulose acetate phthalate, hydroxypropyl methyl cellulose phthalate, biodegradable polymers, copolymers, block polymers, poly(glycolic acid) (PGA), poly(lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), stereopolymers of L- and D-lactic acid, copolymers of bis($\alpha$-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates, cellulose ethers, polymethacrylates, poloxamers, extrudable carbohydrates, acrylates, cellulose acetate butyrate, poly(ethylene-co-vinyl acetate), polyvinyl acetate, poly(methylvinyl ether/maleic anhydride) co-polymer, cellulose acetate phthalate, acrylic polymers, vinylacetate, sodium sulphonated polyesters, carboxylated acrylics, trimethylpentanediol/adipic acid/glycerin cross polymer, polyglycerol-2-diisostearate/IPDI copolymer, carboxylated vinyl acetate copolymer, vinylpyrrolidone/vinyl acetate/alkylaminoacrylate polymers, vinylpyrrolidone/vinyl acetate copolymer, equivalents, or combinations thereof.

Plasticizer(s) can be included in embodiments to produce or promote plasticity and flexibility and to reduce brittleness of the dosage delivery film. Illustrative examples of the plasticizer(s) suitable for use in embodiments of the dosage delivery film composition can be selected from the group including or consisting of: glycerol, glycerol monoacetate, diacetate, triacetate, triacetin, cetyl alcohol, propylene glycol, sorbitol, sodium diethylsulfosuccinate, triethyl citrate, tributyl citrate, glycerin triacetate, equivalents, or combinations thereof.

An anti-foam agent or defoamer can be included in embodiments of the dosage delivery film composition to reduce or hinder the formation of foam during production of intermediate chemical entities or during forming of the production of the dosage delivery film from the dosage delivery film composition. As illustrative examples, defoamer(s) suitable for use in embodiment of the dosage delivery film composition can be selected from the group including or consisting of: simethicone, polydimethylsiloxane, polyethylene glycol, fatty alcohols, fatty acid soaps, fatty acid esters, BREVIOL® equivalents, or combinations thereof.

Antioxidants can be included in embodiments of the dosage delivery film composition to reduce or hinder oxidation during production of intermediate chemical entities or products in the production dosage delivery film. As illustrative examples, antioxidants suitable for use in embodiments of the dosage delivery film composition can be selected from the group including or consisting of: citric acid, butylated hydroxytoluene, ascorbic acid, malonic acid, succinic acid, fumaric acid, maleic acid, adipic acid, lactic acid, levulinic acid, glutamic acid, aspartic acid, oleic acid, glutaric acid, taratic acid, malic acid, sorbic acid, glutathione, retinol, α-tocopherol, β-carotene, α-carotene, γ-tocopherol, ubiquinone, butylated hydroxyanisole, ethylene-diaminetetraacetic acid, selenium, zinc, lignin, uric acid, lipoic acid, and N-acetylcysteine, equivalents, or combinations thereof.

Taste masks can, but need not necessarily, be included in embodiments of the dosage delivery film composition to mask taste of the dosage delivery film produced from the dosage delivery film composition. As illustrative examples, the taste mask can, but need not necessarily, be selected from the group of sweeteners including or consisting of: monosaccharides, disaccharides, polysaccharides, xylose, ribose, glucose, mannose, galactose, fructose, sucrose, high fructose corn syrup, maltose, corn syrup solids, dihydrochalcones, ASPARTAME®, SPLENDA®, SUCRALOSE®, Thaurnatin I, Thaurnatin II, Lo Han Kuo, STEVIA®, steviosides, monellin, glycyrrhizin, a water-soluble sweetening agent, a water-soluble artificial sweetener, a dipeptide-based sweetener, a protein-based sweetener, equivalents, or combinations thereof.

A vasodilator can, but need not necessarily, be included in embodiments of the dosage delivery film composition. As illustrative examples, a vasodilator suitable for use in embodiments of the dosage delivery composition can, but need not necessarily, be menthol, whether synthetic or obtained by processing corn mint, peppermint, or other mint oils, equivalents, or combinations thereof.

A lipophilic carrier can, but need not necessarily, be included in embodiments of the dosage delivery film composition. As illustrative examples, a lipophilic carrier suitable for use in embodiments of the dosage delivery composition can, but need not necessarily, be menthol, whether synthetic or obtained by processing corn mint, peppermint, or other mint oils, equivalents, or combinations thereof.

Now referring primarily to Table 3, particular embodiments of the dosage delivery film composition comprising, consisting essentially of, or consisting of: a polymer, plasticizer, defoamer, antioxidant and water can be prepared as further described below.

TABLE 3

Dosage Delivery Film Composition.

| Ingredient | Percentage (wt/wt) |
| --- | --- |
| Polymer | 20-50% |
| Plasticizer | 0-5% |
| Defoamer | 0-0.5% |
| Antioxidant | 0-3% |
| Water | 30-60% |

As to particular embodiments, the dosage delivery film composition can include only a polymer and water, or comprise, consist essentially of, or consist of a polymer, water, and one or more of: a plasticizer, a defoamer and an antioxidant.

Now referring primarily to Table 4, another particular embodiment of a dosage delivery film composition can comprise, consist essentially of, or consist of combinations of ingredients of Table 3, which can further include a taste mask or a vasodilator.

TABLE 4

Dosage Delivery Film Composition

| Ingredient | Percentage (wt/wt) |
| --- | --- |
| Polymer | 20-45% |
| Plasticizer | 0-5% |
| Defoamer | 0-0.5% |
| Antioxidant | 0-3% |
| Water | 30-60% |
| Vasodilator | 0-5% |
| Taste Mask | 0-5% |

As to particular embodiments, the dosage delivery film composition can comprise, consist essentially of, or consist of: a polymer, water, and one or more of: a plasticizer, a defoamer, an antioxidant, a vasodilator, and a taste mask.

Additional embodiments of the dosage delivery film composition as above described or as set forth in Table 3 or Table 4 can further include a cannabinoid dosage either as a CTC complex as above described or set forth in Table 1 or a cannabinoid micelle as above described or as set forth in Table 2 or as a combination of CTC complexes and cannabinoid micelles.

Accordingly, a particular embodiment of the dosage delivery film composition including a cannabinoid dosage in the form of a CTC complex can comprise, consist essentially of, or consist of the combinations of ingredients of Table 5.

TABLE 5

Dosage Delivery Film Composition Including a Cannabinoid Dosage.

| Ingredient | Percentage (wt/wt) |
| --- | --- |
| Polymer | 20-50% |
| Plasticizer | 0-5% |
| Defoamer | 0-0.5% |
| Water | 25-60% |
| Antioxidant | 0-0.5% |
| β-cyclodextrin | 5-50% |
| Cannabinoid | 5-10% |
| Terpene | 0.1-1.0% |

As to particular embodiments, the dosage delivery film composition can comprise, consist essentially of, or consist of a polymer, water, β-cyclodextrin, cannabinoid, and terpene. Additional embodiments of the dosage delivery system film composition can comprise, consist essentially of, or consist of: a polymer, water, β-cyclodextrin, cannabinoid, terpene, and one or more of: a plasticizer, a defoamer and an antioxidant.

A particular embodiment of the dosage delivery film composition including a cannabinoid dosage in the form of a cannabinoid micelle can comprise, consist essentially of, or consist of the combinations of ingredients of Table 6.

TABLE 6

Dosage Delivery Film Composition Including a Cannabinoid Dosage.

| Ingredient | Percentage (wt/wt) |
| --- | --- |
| Polymer | 20-50% |
| Plasticizer | 0-5% |

TABLE 6-continued

Dosage Delivery Film Composition Including a Cannabinoid Dosage.

| Ingredient | Percentage (wt/wt) |
|---|---|
| Defoamer | 0-0.5% |
| Water | 25-60% |
| Antioxidant | 0-0.5% |
| Surfactant | 1-25% |
| Cannabinoid | 5-18% |
| Terpene | 0.1-1.0% |

As to particular embodiments, the dosage delivery film composition can comprise, consist essentially of, or consist of: a polymer, water, a surfactant, a cannabinoid, and a terpene. Additional embodiments of the dosage delivery film composition can comprise, consist essentially of, or consist of a polymer, water, a surfactant, a cannabinoid, terpene, and one or more of: a plasticizer, a defoamer, and an antioxidant.

A particular embodiment of the dosage delivery film composition including a cannabinoid dosage in the form of a CTC complex and a cannabinoid micelle can comprise, consist essentially of, or consist of the combinations of ingredients of Table 7.

TABLE 7

Dosage Delivery Film Composition Including A Cannabinoid Dosage.

| Ingredient | Percentage (wt/wt) |
|---|---|
| Polymer | 14-60.5% |
| Plasticizer | 0-5% |
| Defoamer | 0-0.5% |
| Surfactant | 1-10% |
| Water | 25-60% |
| Antioxidant | 0.02-0.2% |
| Cannabinoid | 1-10% |
| β-cyclodextrin | 4-40% |
| Terpene | 0.1-5% |

In particular embodiments, the dosage delivery film composition can comprise, consist essentially of, or consist of a polymer, water, β-cyclodextrin, an antioxidant, a surfactant, a cannabinoid, and a terpene. Additional embodiments of the dosage delivery film composition can comprise, consist essentially of, or consist of a polymer, water, β-cyclodextrin, an antioxidant, a surfactant, a cannabinoid, a terpene, and one or more of: a plasticizer and a defoamer.

In particular embodiments, the dosage delivery film composition including a cannabinoid dosage as described above and set forth in either Tables 5, 6, or 7, can further comprise, consist essentially of, or consist of an amount of: a taste mask in the form of a sweetener in an amount of about 3% to about 6%, or an amount of vasodilator in the form of menthol of about 0.1% to about 5%, or both.

Accordingly, a particular embodiment of the dosage delivery film composition including a cannabinoid dosage in the form of a combination of a CTC complex and a cannabinoid micelle and further including a taste mask in the form of an amount of sweetener and optionally a vasodilator in the form of an amount of menthol, or both, can comprise, consist essentially of, or consist of the combinations of ingredients of Table 8.

TABLE 8

Dosage Delivery Film Composition Including a Cannabinoid Dosage.

| Ingredient | Percentage (wt/wt) |
|---|---|
| Polymer | 14-60.5% |
| Plasticizer | 2-8% |
| Taste Mask (Sweetener) | 3-6% |
| Defoamer | 0.01-0.2% |
| Surfactant | 1-10% |
| Water | 25-60% |
| Antioxidant | 0.02-0.2% |
| Vasodilator | 0-5% |
| Cannabinoid | 5-40% |
| β-cyclodextrin | 5-20% |
| Terpene | 0.1-1.0% |

A particular embodiment of the dosage delivery film composition including a cannabinoid dosage in the form of a combination of a CTC complex and a cannabinoid micelle, and further including a task mask in the form of an amount of sweetener and optionally a vasodilator in the form of an amount of menthol can comprise, consist essentially of, or consist of the combination of ingredients of Table 9.

TABLE 9

Dosage Delivery Film Composition Including a Cannabinoid Dosage.

| Ingredient | Percentage (wt/wt) |
|---|---|
| Polyethylene Glycol | 0-15% |
| Hydroxypropylmethyl cellulose | 0-0.5% |
| Polyvinyl Alcohol | 5-50% |
| Glycerol | 2-8% |
| Taste Mask (sucrose) | 3-6% |
| Polydimethoxysilane | 0.01-0.2% |
| Polyethylene glycol sorbitan monooleate | 1-10% |
| Water | 25-60% |
| Beta-carotene | 0.02-0.2% |
| Vasodilator (Menthol) | 0-5% |
| Polyvinylpyrrolidone | 0-20% |
| Cannabinoid | 5-40% |
| β-cyclodextrin | 5-20% |
| Terpene | 0.1-1.0% |

In particular embodiments, the polyvinyl alcohol can be hydrolyzed between about 84% to about 89%. Further, the average molecular weight of the polyvinyl alcohol can be between about 25,000 Daltons (Da) and about 78,000 Da. The average molecular weight of the polyvinyl alcohol can be selected from the group including or consisting of: about 26,000 Da to about 30,000 Da, about 27,500 Da to about 28,250 Da, about 30,000 Da to about 35,000 Da, about 32,500 Da to about 37,500 Da, about 35,000 Da to about 40,000 Da, about 37,500 Da to about 42,500 Da, about 40,000 Da to about 45,000 Da, about 42,500 Da to about 47,500 Da, about 45,000 Da to about 50,000 Da, about 47,500 Da to about 52,500 Da, about 50,000 Da to about 55,000 Da, about 52,500 Da to about 57,500 Da, about 55,000 Da to about 60,000 Da, about 57,500 Da to about 62,500 Da, about 60,000 Da to about 65,000 Da, about 62,500 Da to about 67,500 Da, about 65,000 Da to about 70,000 Da, about 67,500 Da to about 72,500 Da, about 70,000 Da to about 75,000 Da, and about 72,500 Da to about 77,000 Da, or combinations thereof.

In particular embodiments, the polyethylene glycol can have an average molecular weight of about 1000 Da to about 1600 Da. The average molecular weight of the polyethylene glycol can be selected from the group including or consisting of: about 1025 Da to about 1075 Da, about 1050 Da to about 1100 Da, about 1075 Da to about 1125 Da, about 1100 Da to about 1150 Da, about 1125 Da to about 1175 Da, about 1150 Da to about 1200 Da, about 1175 Da to about 1225 Da, about 1200 Da to about 1250 Da, about 1225 Da to about 1275 Da, about 1250 Da to about 1300 Da, about 1275 Da to about 1325 Da, about 1300 Da to about 1350 Da, about 1325 Da to about 1375 Da, about 1350 Da to about 1400 Da, about 1375 Da to about 1425 Da, about 1400 Da to about 1450 Da, about 1425 Da to about 1475 Da, about 1450 Da to about 1500 Da, about 1475 Da to about 1525 Da, about 1500 Da to about 1550 Da, and about 1525 Da to about 1575 Da, or combinations thereof.

In particular embodiments, the polyvinylpyrrolidone can have an average molecular weight between about 20,000 Da and about 40,000 Da. The average molecular weight of the polyvinylpyrrolidone can be selected from the group including or consisting of: about 21,000 Da to about 23,000 Da, about 22,000 Da to about 24,000 Da, about 23,000 Da to about 25,000 Da, about 24,000 Da to about 26,000 Da, about 25,000 Da to about 27,000 Da, about 26,000 Da to about 28,000 Da, about 27,000 Da to about 29,000 Da, about 28,000 Da to about 30,000 Da, about 29,000 Da to about 31,000 Da, about 30,000 Da to about 32,000 Da, about 31,000 Da to about 33,000 Da, about 32,000 Da to about 34,000 Da, about 33,000 Da to about 35,000 Da, about 34,000 Da to about 36,000 Da, about 35,000 Da to about 37,000 Da, about 36,000 Da to about 38,000 Da, and about 37,000 Da to about 39,000 Da, or combinations thereof.

The following working examples are intended to illustrate a method of making the dosage delivery film composition containing a dosage of cannabinoid carried by the first or second carriers, as above described.

Example 1. Preparation of Cannabinoid Micelles

A cannabinoid micelle in accordance with embodiments can be prepared by combining in the weight percentages above described in Table 2 of cannabinoid and terpene in ethanol, and further combining this solution with the surfactant in water. The combination of ingredients incubated at about 20° C. to about 25° C. for a period of about 1 hour to about 4 hours to produce cannabinoid micelles.

Example 2. Preparation of CTC Complexes

A CTC complex in accordance with embodiments can be prepared by combining in the weight percentages above described in Table 1 of cannabinoid and terpene in ethanol, and further combining this solution with β-cyclodextrin in water. The combination of ingredients is incubated at about 20° C. to about 25° C. for a period of about 1 hour to about 4 hours to produce the CTC complex. As to particular embodiments, the CTC complex can be rendered as a solid by lyophilization. As to particular embodiments, the CTC complex may form a precipitate which can be captured by filtration of the solution.

Example 3. Preparation of CTC Complexes and Cannabinoid Micelles

A CTC complex in accordance with embodiments and a cannabinoid micelle in accordance with embodiments can be prepared by combining cannabinoid and terpene in ethanol, and further combining the solution with β-cyclodextrin and surfactant in water in the weight percentages or ratios of weight percentages described above. The combination of ingredients incubated at about 20° C. to about 25° C. for a period of about 1 hour to about 4 hours. The solution will contain a mixture of CTC complexes and cannabinoid micelles which can remain discrete in solution or can associate in solution to form CTC complex-cannabinoid micelle complexes.

Example 4. Preparation of the Dosage Delivery Film Composition

Dosage delivery film compositions in accordance with embodiments can be prepared by combining in the weight percentages above described in Table 3 or Table 4, a polymer (such as polyethylene glycol, hydroxypropylmethylcellulose or polyvinylpyrrolidone), a plasticizer (such as glycerol), optionally a taste mask (such as sucrose), in a portion of the water (such as deionized or distilled water). The ingredients are mixed at 80° C. until all ingredients have dissolved. A second solution can be prepared by combining in the weight percentages above described in Table 3 or Table 4, a polymer (such as polyvinyl alcohol), and defoamer (such as polydimethylsiloxane) in a portion of the water (such as deionized or distilled). The ingredients are mixed at 60° C. until all the ingredients have dissolved. The first solution can be mixed with the second solution at a temperature of about 60° C. for about 15 to about 30 minutes.

Example 5. Preparation of the Dosage Delivery Film Composition Including a Cannabinoid Dosage A dosage delivery film composition in accordance with embodiments including, but not limited to, the compositions of Table 5 through 9 can be prepared by combining in the weight percentages above described in a first solution polyethylene glycol, hydroxypropylmethylcellulose, polyvinylpyrrolidone, glycerol (each a polymer), and optionally sucrose (a taste mask) in a portion of the water. The ingredients are mixed at 80° C. until all ingredients have dissolved. A second solution can be prepared by combining in the weight percentages above described polyvinyl alcohol (a polymer), and polydimethylsiloxane (a defoamer), in a portion of the water. The ingredients are mixed at 60° C. until all the ingredients have dissolved. A third solution can be prepared by combining in the weight percentages above described polyethylene glycol sorbitan monooleate (a surfactant), cannabinoid, β-cyclodextrin, beta-carotene (an antioxidant), menthol (a vasodilator or lipohilic vehicle), terpene (an anesthetic, sedative, or aromatic or combinations thereof), and polyvinylpyrrolidone (a polymer). The ingredients are mixed at about 20° C. to about 25° C. until all ingredients are dissolved. The ethanol can be evaporated from the solution using a rotary evaporator with a bath temperature of about 50° C.

The first solution can be mixed with the second solution at a temperature of about 60° C. for about 15 minutes to about 30 minutes. The third solution can then be added to the first and second solution with vigorous mixing at 60° C. for about 15 minutes to about 35 minutes. In some circumstances, the resulting combined mixture of the first, second, and third solutions can further undergo rotary evaporation to remove excess ethanol.

As can be easily understood from the foregoing, the basic concepts of the present invention may be embodied in a variety of ways. The invention involves numerous and varied embodiments of a dosage delivery film and methods for making and using such dosage delivery films including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "dosage" should be understood to encompass disclosure of the act of "dosing"—whether explicitly discussed or not—and, conversely, were there effectively disclosure of the act of "dosing", such a disclosure should be understood to encompass disclosure of a "dosage" and even a "means for dosing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the dosage delivery films herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

With respect to the formulations provided in this description, it should be understood that different formulations can contain the same raw materials, but can be distinguished by the difference in the weight percent of each of the raw materials. Specific difference in weight percent of each raw material between formulations can impart different functional characteristics or property to the dosage delivery film. Accordingly, it will be understood that each particular weight percent value for a raw material can form another embodiment of the dosage delivery film.

Also, it is to be understood that the ranges established by the differences of the particular weight percent values for each raw material can include the outliers in the normal variation of each particular value necessary to achieve one or more particular functional characteristics or can be the variation inherent to the manufacturing process of a particular formulation. Accordingly, a value range can describe either a single embodiment having a formulation that can vary as to any particular raw material between the particular weight percent values, or two different liquid cleaners differentiated by the extremes of the weight percent values of each raw material, each extreme having the normal degree of variation based on manufacturing practices, or a plurality of different embodiments, each having a discrete formulation which includes a weight percent value of each raw material which falls in the range of weight percent values established by the difference in weight percent values (with normal variation in weight percent due to the manufacturing process). Additionally, each particular value listed is not intended to be interpreted solely as an absolute value but is also intended to include in the alternative an embodiment which includes the term "about" for the particular value, as that term is described above.

Generally, as to each of the formulation set out herein, each particular weight percent value shall not be interpreted solely as an absolute value and each particular weight percent value as to each raw material will be interpreted as having a range between a first particular weight percent value and second particular weight percent value based upon normal variation in the manufacturing process of the formulation, these ranges may be expressed herein as from "about" one particular value to "about" another particular value. When such a range is expressed, another embodiment includes from the particular value to the other particular value. Similarly, when values are expressed as approximations, by use of the antecedent "about," it will be understood that the particular value forms another embodiment. It will further be understood that the endpoints of each of the ranges are significant both in relation to the other endpoint, and independently of the other endpoint.

I claim:

1. An orally administered drug delivery film, comprising:
   a polymer of about 20% to about 50%;
   a plasticizer of about 6% to about 9%;
   a defoamer of about 0.2% to about 0.5%;
   an antioxidant of about 0% to about 3%;
   a β-cyclodextrin; and
   a cannabinoid;
      wherein a first portion of said cannabinoid comprises a cannabinoid-β-cyclodextrin complex,
      wherein a second portion of said cannabinoid comprises a micelle,
         wherein said micelle having a hydrophobic core of said cannabinoid and a hydrophilic shell of a surfactant; and
   water of about 30% to about 60%.

2. The orally administered drug delivery film of claim 1, wherein said polymer is selected from the group consisting of: polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, xanthan gum, tragancanth gum, guar gum, acacia gum, arabic gum, polyacrylic acid, methylmethacrylate copolymer, carboxyvinyl copolymers, starch, gelatin, ethyl cellulose, hydroxypropyl ethyl cellulose, cellulose acetate phthalate, hydroxypropyl methyl cellulose phthalate, poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates, cellulose ethers, polymethacrylates, poloxamers, extrudable carbohydrates, acrylates, cellulose acetate butyrate, poly(ethylene-co-vinyl acetate), polyvinyl acetate, poly(methylvinyl ether/maleic anhydride) co-polymer, cellulose acetate phthalate, acrylic polymers, vinylacetate, sodium sulphonated polyesters, carboxylated acrylics, trimethylpentanediol/adipic acid/glycerin cross polymer, polyglycerol-2-diisostearate/IPDI copolymer, carboxylated vinyl acetate copolymer, vinylpyrrolidone/vinyl acetate/alkylaminoacrylate polymers, vinylpyrrolidone/vinyl acetate copolymer, and combinations thereof.

3. The orally administered drug delivery film of claim 1, wherein said polymer comprises one or more of: polyethylene glycol, hydroxypropylmethylcellulose, polyvinylpyrrolidone, and polyvinyl alcohol.

4. The orally administered drug delivery film of claim 2, wherein said polyvinyl alcohol comprises polyvinyl alcohol hydrolyzed between about 84% to about 89% and having an average molecular weight of between about 25,000 Daltons (Da) to about 78,000 Da.

5. The orally administered drug delivery film of claim 1, wherein said plasticizer is selected from the group including or consisting of: glycerol, glycerol monoacetate, glycerol diacetate, glycerol triacetate, triacetin, cetyl alcohol, propylene glycol, sorbitol, sodium diethylsulfosuccinate, triethyl citrate, tributyl citrate, glycerin triacetate, or combinations thereof.

6. The orally administered drug delivery film of claim 1, wherein said plasticizer comprises one or more of: glycerol and glycerin triacetate.

7. The orally administered drug delivery film of claim 1, wherein said defoamer is selected from the group consisting of: simethicone, polydimethylsiloxane, polyethylene glycol, fatty alcohols, fatty acid soaps, fatty acid esters, and combinations thereof.

8. The orally administered drug delivery film of claim 1, wherein said defoamer comprises polydimethylsiloxane.

9. The orally administered drug delivery film of claim 1, wherein said antioxidant is selected from the group consisting of: citric acid, butylated hydroxytoluene, ascorbic acid, malonic acid, succinic acid, fumaric acid, maleic acid, adipic acid, lactic acid, levulinic acid, glutamic acid, aspartic acid, oleic acid, glutaric acid, taratic acid, malic acid, sorbic acid, glutathione, retinol, α-tocopherol, β-carotene, α-carotene, γ-tocopherol, ubiquinone, butylated hydroxyanisole, ethylene-diaminetetraacetic acid, selenium, zinc, lignin, uric acid, lipoic acid, and N-acetylcysteine, beta-carotene equivalents, or combinations thereof.

10. The orally administered drug delivery film of claim 1, wherein said antioxidant comprises one or more of: beta-carotene, tocopherol, and vitamin E.

11. The orally administered drug delivery film of claim 1, further comprising a taste mask of about 0% to about 5%.

12. The orally administered drug delivery film of claim 11, wherein said taste mask is selected from the group consisting of: monosaccharides, disaccharides, polysaccharides, xylose, ribose, glucose, mannose, galactose, fructose, sucrose, high fructose corn syrup, maltose, corn syrup solids, dihydrochalcones, Thaurnatin I, Thaurnatin II, Lo Han Kuo, steviosides, monellin, glycyrrhizin, equivalents, or combinations thereof.

13. The orally administered drug delivery film of claim 11, wherein said taste mask comprises one or more of sucrose, glucose and maltose.

14. The orally administered drug delivery film of claim 1, further comprising a vasodilator of about 0% to about 5%.

15. The orally administered drug delivery film of claim 14, wherein said vasodilator comprises menthol, whether synthetic or obtained by processing corn mint, peppermint, or other mint oils, equivalents, and combinations thereof.

16. The orally administered drug delivery film of claim 1, further comprising a terpene of about 0.1% to about 1%.

17. The orally administered drug delivery film of claim 16, wherein said terpene is selected from the group consisting of: alpha-pinene, beta-pinene, myrcene, limonene, carophyllene, linalool, alpha bisabolol, delta 3 carene, borneol, eucalyptol, terpineol, camphene, nerolidol, terpinolene, valencene, humulene, geraniol, phellandrene, fenchol, phytol, sabinene, camphor, menthol, isoborneol, cedrane, guaiol, isopulegol, geranyl acetate, cymene, pulegon, citral, or combinations thereof.

18. The orally administered drug delivery film of claim 1, wherein said cannabinoid selected from the group consisting of: cannabinol, cannabinolic acid, Δ(9)-tetrahydrocannabinol, Δ(9)-tetrahydrocannabinolic acid, Δ(9)-cannabidiol, Δ(9)-tetrahydrocannabidiolic acid, Δ(8)-tetrahydrocannabinol, Δ(8)-tetrahydrocannabinolic acid, Δ(8)-tetrahydrobannabidiol, Δ(8), tetrahydrocannacbidiolic acid, Δ(9)-tetrahydrocannabivarin, cannabigerol, cannabidigerolic acid, cannabichromene, cannabichromenic acid, cannabicyclol, cannabicyclolic acid, cannabielsoin, cannabitriol, Nabilone, or combinations thereof.

19. The orally administered drug delivery film of claim 1, wherein said amount of cannabinoid associated with β-cyclodextrin in a wt/wt ratio of between about 1:1 to about 1:4.

20. The orally administered drug delivery film of claim 19, wherein said β-cyclodextrin is selected from the group consisting of: hydroxypropyl-β-cyclodextrin, sulfobutylether-β-cyclodextrin, maltosyl-β-cyclodextrin, dimethyl-β-cyclodextrin, trimethyl-β-cyclodextrin, randomly methylated-β-cyclodextrin, or combinations thereof.

21. The orally administered drug delivery film of claim 19, wherein said β-cyclodextrin comprises one or more of: randomly methylated-β-cyclodextrin or hydroxypropyl-β-cyclodextrin.

22. The orally administered drug delivery film of claim 1, wherein said surfactant of about 1% to about 10%.

23. The orally administered drug delivery film of claim 22, wherein said surfactant selected from the group consisting of: monoglycerides, diglycerides, polyethylene glycol sorbitan fatty acid esters; polyethylene glycol alkyl ethers, phospholipids, hydrophilic derivatives of phospholipids, PEG-40 castor oil, PEG-60 corn glycerides, vitamin E, TWEEN 80, polyoxyethylene alkyl ethers, polyethylene glycol glycerol fatty acid esters, polyoxyethylene sorbitan fatty acid esters, or combinations thereof.

24. An orally administered drug delivery film, comprising:
a polymer of about 20% to about 50%;
a plasticizer of about 6% to about 9%;
a defoamer of about 0.2% to about 0.5%;
an antioxidant of about 0% to about 3%;
a β-cyclodextrin;
a cannabinoid;
  wherein a first portion of said cannabinoid comprises a cannabinoid-β-cyclodextrin complex,
  wherein a second portion of said cannabinoid comprises a micelle,
    wherein said micelle having a hydrophobic core of between about five to about fifty molecules of said cannabinoid and a hydrophilic shell of a surfactant, wherein said micelle has a diameter of between about 40 nm to about 100 nm; and
water of about 30% to about 60%.

25. An orally administered drug delivery film, comprising:
a polymer of about 20% to about 50%;
a plasticizer of about 6% to about 9%;
a defoamer of about 0.2% to about 0.5%;
an antioxidant of about 0% to about 3%;
a β-cyclodextrin;
a surfactant of about surfactant of about 1% to about 10%;
a cannabinoid;
  wherein a first portion of said cannabinoid comprises a cannabinoid-β-cyclodextrin complex,
  wherein a second portion of said cannabinoid comprises a micelle,
    wherein said micelle having a hydrophobic core of between about five to about fifty molecules of said cannabinoid and a hydrophilic shell of said surfactant, wherein said micelle having a diameter of between about 40 nm to about 100 nm; and
water of about 30% to about 60%.

26. An orally administered drug delivery film, comprising:
a polymer of about 20% to about 50%;
a plasticizer of about 6% to about 9%;
a defoamer of about 0.2% to about 0.5%;
an antioxidant of about 0% to about 3%;
a β-cyclodextrin;
a surfactant of about surfactant of about 1% to about 10%;
a cannabinoid;
  wherein a first portion of said cannabinoid comprises a cannabinoid-β-cyclodextrin complex,
    wherein said first portion of said cannabinoid associated with β-cyclodextrin having a wt/wt ratio of between about 1:1 to about 1:4; and
  wherein a second portion of said cannabinoid comprises a micelle,
    wherein micelle having a hydrophobic core of between about five to about fifty molecules of said cannabinoid and a hydrophilic shell of said surfactant, wherein said micelle having a diameter of between about 40 nm to about 100 nm; and
water of about 30% to about 60%.

27. The orally administered drug delivery film of claim 1, wherein in a first mixture a portion of said polymer, said plasticizer and optionally a taste mask combined in a portion of said water under heat until dissolved;

wherein in a second mixture a portion of said polymer, said defoamer combined in a portion of said water under heat until dissolved; and wherein said first mixture combined with said second mixture.

28. The orally administered drug delivery film of claim 27, wherein said first mixture, said polymer comprises one or more of polyethylene glycol, hydroxypropylmethylcellulose and polyvinylpyrrolidone, said plasticizer comprises glycerol, and said taste mask comprises sucrose, and wherein in said second mixture said polymer comprises as polyvinyl alcohol, and said defoamer comprises polydimethylsiloxane.

29. The orally administered drug delivery film of claim 28, wherein in a third mixture, said polymer, said surfactant, said cannabinoid, said β-cyclodextrin, said antioxidant, and optionally a vasodilator and a terpene, combined in an amount of ethanol.

30. The orally administered drug delivery film of claim 29, wherein said surfactant comprises polyethylene glycol sorbitan monooleate, said polymer comprises polyvinylpyrrolidone, said antioxidant comprises beta-carotene, and said vasodilator comprises menthol.

31. The orally administered drug delivery film of claim 29, wherein said third mixture combined with said first and second mixture.

32. The orally administered drug delivery film of claim 1, wherein said micelle having a hydrophobic of said cannabinoid and a hydrophilic shell of a surfactant, wherein said micelle having a diameter of between about 40 nm to about 100 nm.

* * * * *